United States Patent
Yan et al.

(10) Patent No.: US 12,156,747 B2
(45) Date of Patent: Dec. 3, 2024

(54) TABLE SUPPORT FOR A MOBILE IMAGING SYSTEM

(71) Applicant: GE Precision Healthcare LLC, Wauwatosa, WI (US)

(72) Inventors: Weiji Yan, Beijing (CN); Jiaqi Li, Waukesha, WI (US); Zheng Lu, Beijing (CN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 360 days.

(21) Appl. No.: 17/650,660

(22) Filed: Feb. 10, 2022

(65) Prior Publication Data

US 2023/0248316 A1 Aug. 10, 2023

(51) Int. Cl.
*A61B 5/00* (2006.01)
*A61B 5/055* (2006.01)

(52) U.S. Cl.
CPC .............. *A61B 5/704* (2013.01); *A61B 5/055* (2013.01)

(58) Field of Classification Search
CPC ....... A61B 5/704; A61B 5/055; A61B 6/0442; A61B 5/70; A61B 5/702; B64D 2011/0092; A61G 1/06; A61G 3/0858; A61G 3/0825
See application file for complete search history.

(56) References Cited

U.S. PATENT DOCUMENTS

| | | | | |
|---|---|---|---|---|
| 5,727,353 A * | 3/1998 | Getz | ................. | A61B 6/4405 62/223 |
| 6,024,528 A * | 2/2000 | Taylor | ................. | A61G 3/062 414/921 |
| 9,186,288 B2 * | 11/2015 | Sartin | ................. | B60R 11/00 |
| 9,241,850 B2 * | 1/2016 | Chinn | ................. | A61G 3/006 |
| 9,375,187 B2 | 6/2016 | Etters | | |
| 9,700,265 B2 | 7/2017 | Eder et al. | | |
| 9,814,432 B2 | 11/2017 | Igney et al. | | |
| 10,457,376 B1 * | 10/2019 | Koman | ................. | B64C 1/20 |
| 2009/0255058 A1 * | 10/2009 | Chinn | ................. | A61G 3/085 5/118 |
| 2010/0045059 A1 * | 2/2010 | Bourgraf | ................. | A61G 3/029 296/19 |
| 2016/0092078 A1 | 3/2016 | Braun et al. | | |
| 2017/0112694 A1 * | 4/2017 | Naber | ................. | A61G 3/0254 |
| 2019/0343291 A1 * | 11/2019 | Avegno | ................. | A47C 1/0342 |
| 2020/0150760 A1 | 5/2020 | Lorkowski et al. | | |
| 2022/0008016 A1 * | 1/2022 | Harrison | ................. | A61G 3/001 |

FOREIGN PATENT DOCUMENTS

CN 110833412 A 2/2020

* cited by examiner

*Primary Examiner* — Myles A Throop
(74) *Attorney, Agent, or Firm* — McCoy Russell LLP

(57) ABSTRACT

Various methods and systems are provided for a table support for a mobile imaging system. In one example, a table support for a mobile imaging system includes a fixture comprising a frame and a plurality of posts coupled to the frame, a table interface comprising a set of table flanges configured to be attached to a patient table of the mobile imaging system and a set of complementary table flange acceptors coupled to a top surface of the frame of the fixture, and a floor interface including a set of floor brackets removably coupleable to a set of floor panels configured to be attached to a floor of a unit configured to house the mobile imaging system, each floor bracket coupled to two respective posts of the plurality of posts.

20 Claims, 12 Drawing Sheets

TABLE SUPPORT FOR A MOBILE IMAGING SYSTEM

FIELD

Embodiments of the subject matter disclosed herein relate to mobile imaging systems, and more particularly, to a patient table support for a mobile imaging system.

BACKGROUND

Magnetic resonance imaging (MRI) is a medical imaging modality that can create images of the inside of a human body without using x-rays or other ionizing radiation. MRI systems typically include a patient table configured to support a patient within a bore during imaging. The patient table may include components for facilitating MR imaging within the table, such as radio frequency (RF) coils.

BRIEF DESCRIPTION

In one embodiment, a table support for a mobile imaging system includes a fixture comprising a frame and a plurality of posts coupled to the frame, a table interface comprising a set of table flanges configured to be attached to a patient table of the mobile imaging system and a set of complementary table flange acceptors coupled to a top surface of the frame of the fixture, and a floor interface including a set of floor brackets removably coupleable to a set of floor panels configured to be attached to a floor of a unit configured to house the mobile imaging system, each floor bracket coupled to two respective posts of the plurality of posts.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to various embodiments for a table support usable to transport a patient table. The patient table may be relatively heavy and may include electronics to facilitate imaging. As such, it may be desired to reduce vibrations incurred during transportation with a table support coupled between the patient table and a floor/ground on which the table sits during transportation (e.g., a trailer). However, conventional table supports include multiple fixtures and require a complex, multi-step installation and uninstallation procedure, thus costing excess time that could be used to image a patient, for example.

Thus, a "slide and go" table support including only a single fixture is disclosed herein. The table support of the present disclosure may include a three-part design including a table interface, a single fixture, and a floor interface. During installation of the table support, the patient table may be raised and the fixture may be positioned under a rear portion of the table. The table may then be lowered to rest on the fixture, via the table interface. The table interface may include two components directly attached to an underside of the patient table that fit into complementary components attached to a top side of the fixture. The fixture may have a frame with an H-shaped design and four posts coupled to the frame that can support the heavy patient table without cracking. The fixture may be secured to the floor via the floor interface, which may include two panels attached to the floor that include locking pockets into which clamps on the fixture may be secured, avoiding the need for loose screws.

The table support described herein may be used to support a patient table of a magnetic resonance imaging (MRI) system, as will be elaborated herein. However, the table support may be used to support other heavy tables, such patient tables for use in computed tomography (CT) imaging, tomosynthesis, positron emission tomography (PET), C-arm angiography, and so forth. The present discussion of an MRI modality is provided merely as an example of one suitable imaging modality that includes a patient table that may be supported by the table support of the present disclosure.

Figure 1:
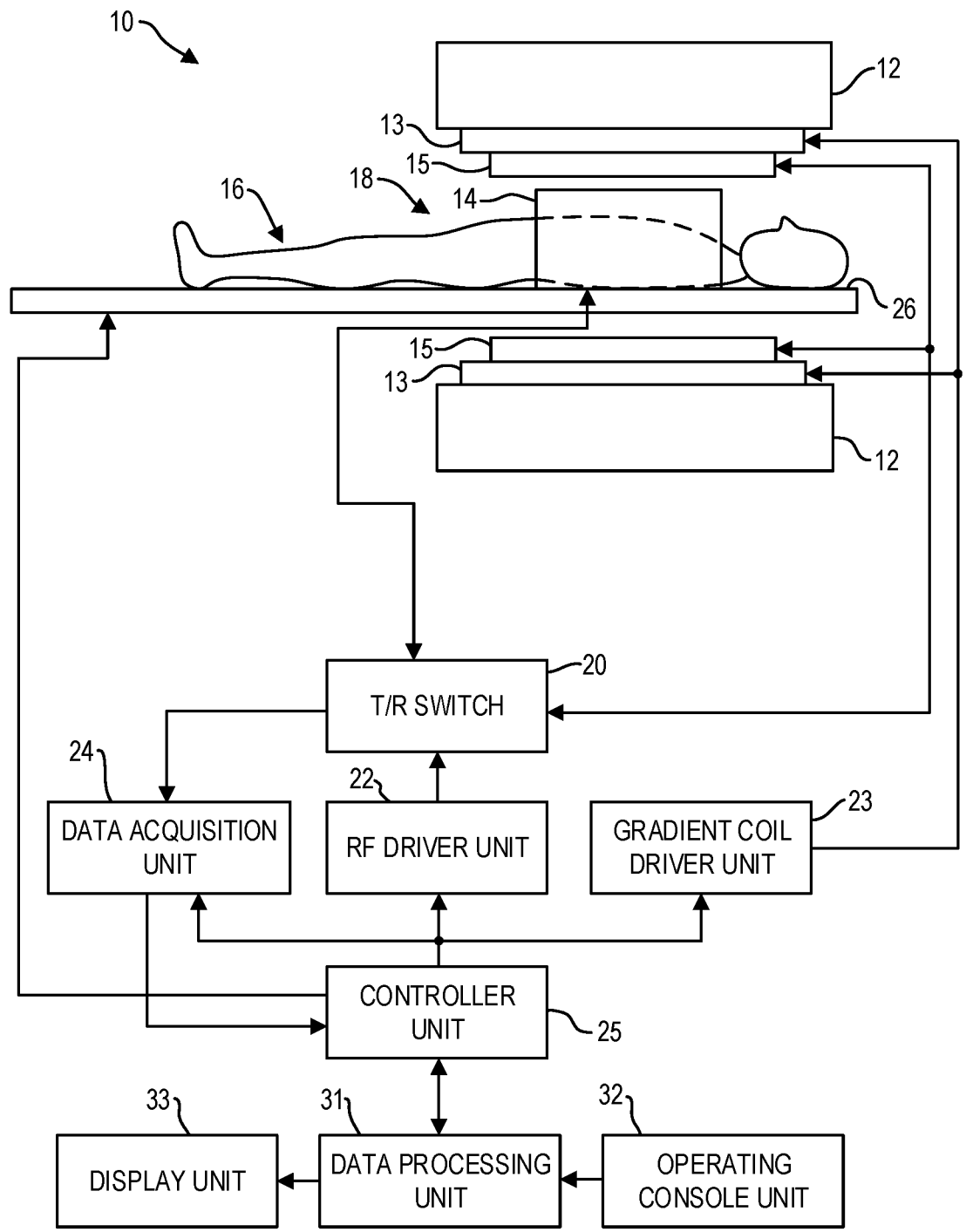
FIG. 1 is a block diagram of an MRI system according to an embodiment of the disclosure.

FIG. 1 illustrates an MRI apparatus 10 that includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, a data processing unit 31, an operating console unit 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) image of the subject 16 generated by the data processing unit 31.

In some examples, the MRI apparatus 10 may be a mobile MRI apparatus configured to be transported to various sites, and may not be permanently installed in a building. For example, the MRI apparatus 10 may be positioned in a trailer that can be transported from site to site. During transport of the MRI apparatus 10, the table 26 may be subject to vibrations that may degrade components of the table 26. For example, the table 26 may be heavy owing to the inclusion of aspects of the MRI apparatus 10 within the table 26, such as the RF coil unit 15, and vibration of the table 26 may cause degradation to the table 26 and/or components within the table 26. Thus, prior to transporting the MRI apparatus 10, the table 26 may be secured to a floor of a trailer or other transport unit with a table support, an example of which is shown in FIGS. 2-12.

FIGS. 2-12 show an example of a table support 200 that may be positioned between a patient table, such as table 26 of FIG. 1, and a floor during transport of the patient table. FIGS. 2-12 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. To establish the relative and absolute directions, a coordinate system 201 is included in FIGS. 2-12 which comprises x, y, and z axes. As described herein, the directions "left," "right," "forward," "backward," "up," and "down" represent directions in the negative x, positive x, negative y, positive y, negative z, and positive z, respectively. Similarly, relative positions of objects may be described via the prepositions "left of," "right of," "behind," "in front of," "below," and "above," indicating relative positions in the negative x-axis, positive x-axis, negative y-axis, positive y-axis, negative z-axis, and positive z-axis, respectively. Further, the z-axis is chosen to align with gravity, such that forces due to gravity (e.g. weight) act in the negative z ("down") direction. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Figure 2:
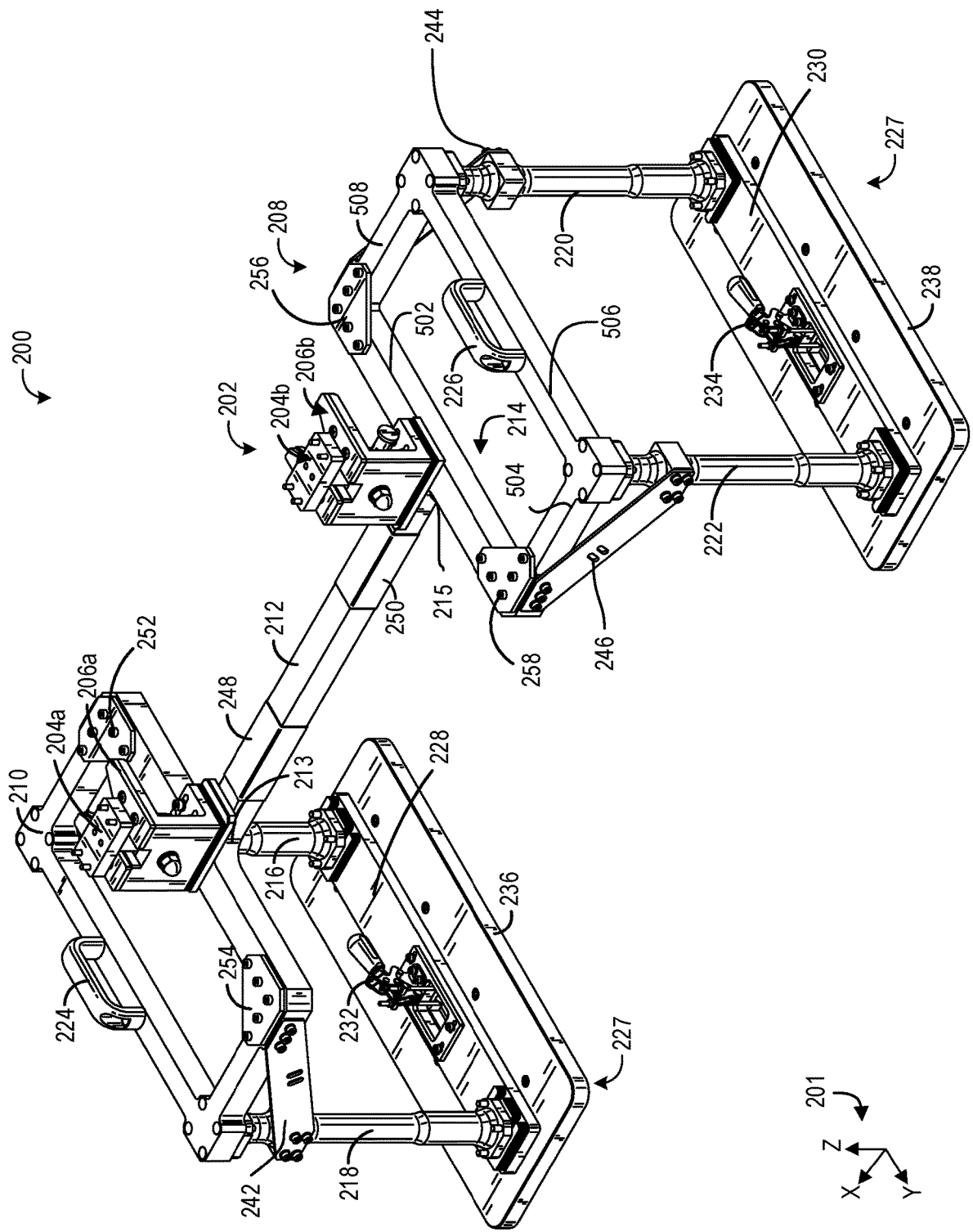
FIG. 2 shows a first perspective view of a patient table support according to an embodiment of the disclosure.
Figure 3:
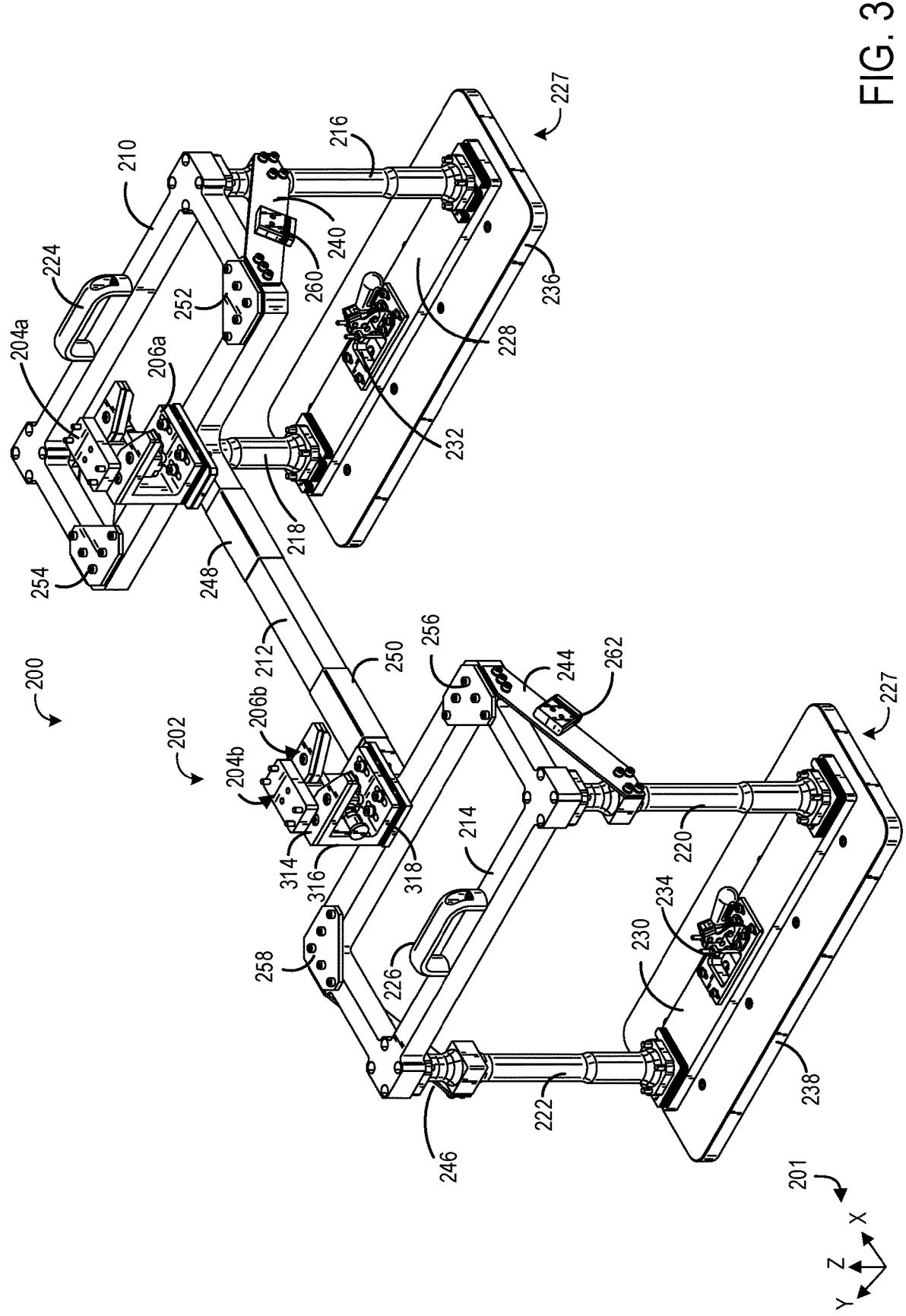
FIG. 3 shows a second perspective view of the patient table support.
Figure 4:
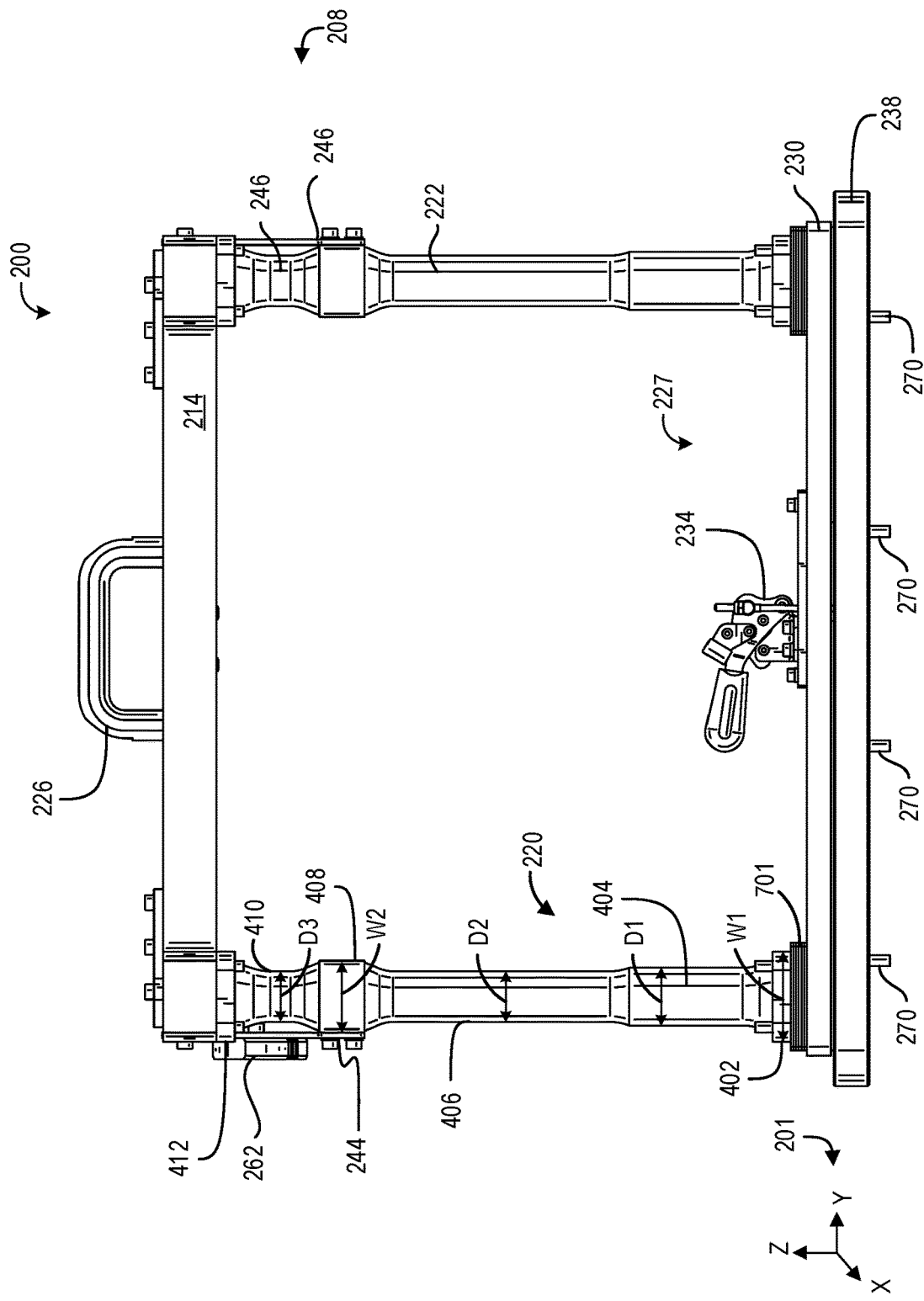
FIG. 4 shows a first side view of the patient table support.
Figure 5:
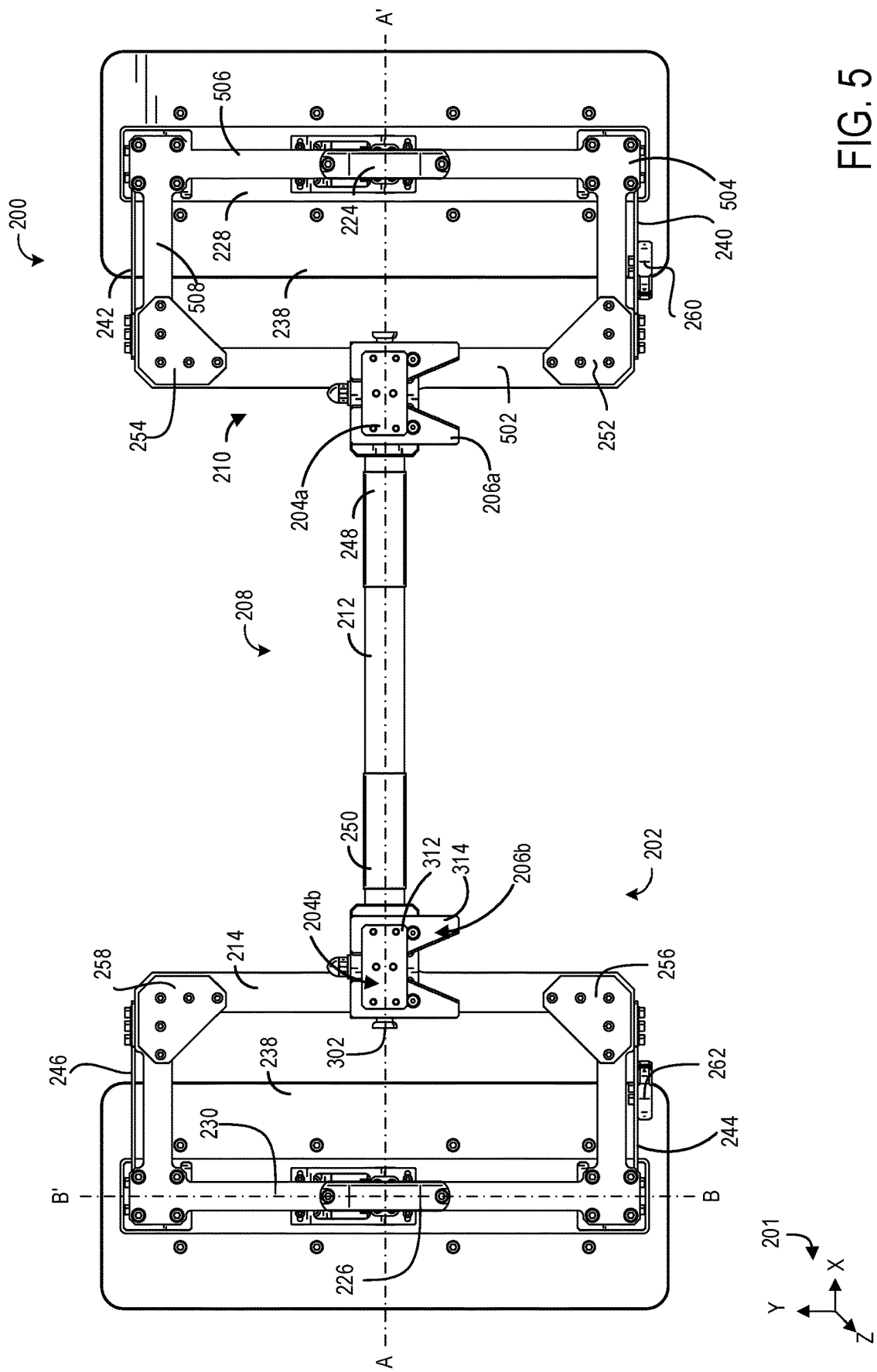
FIG. 5 shows a top-down view of the patient table support.
Figure 6:
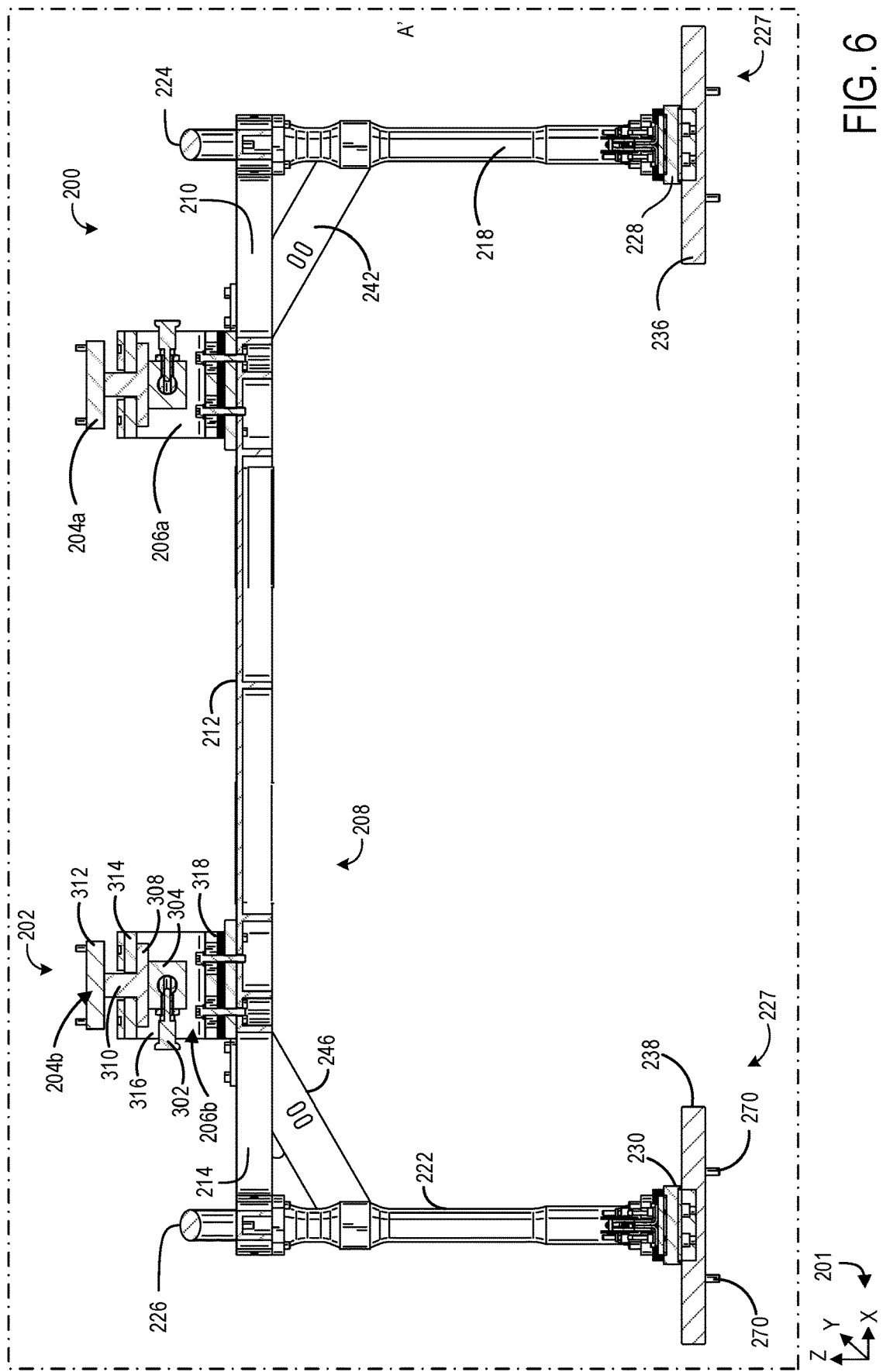
FIG. 6 shows a first cross-sectional view of the patient table support.
Figure 7:
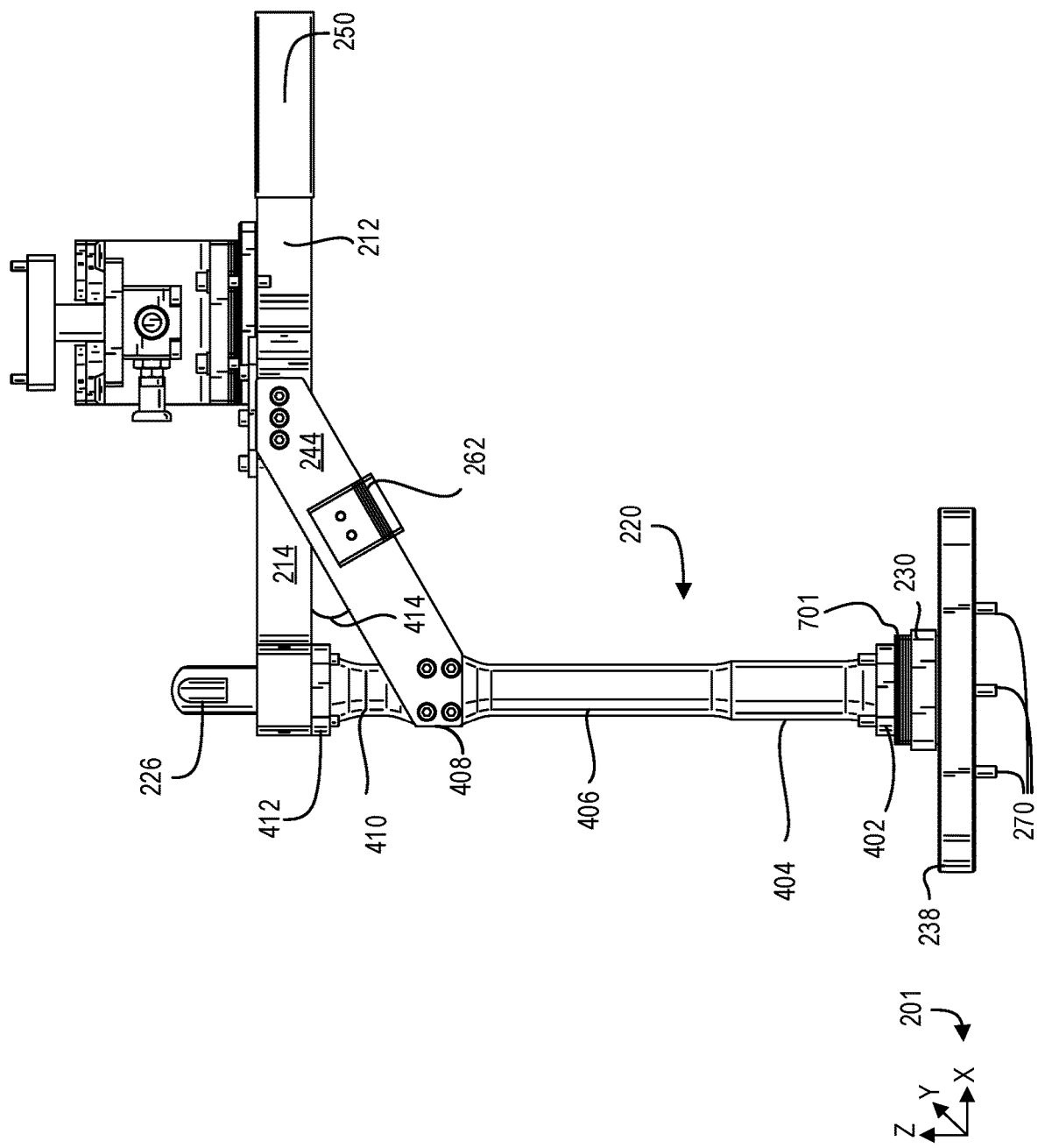
FIG. 7 shows a second side view of the patient table support.
Figure 8:
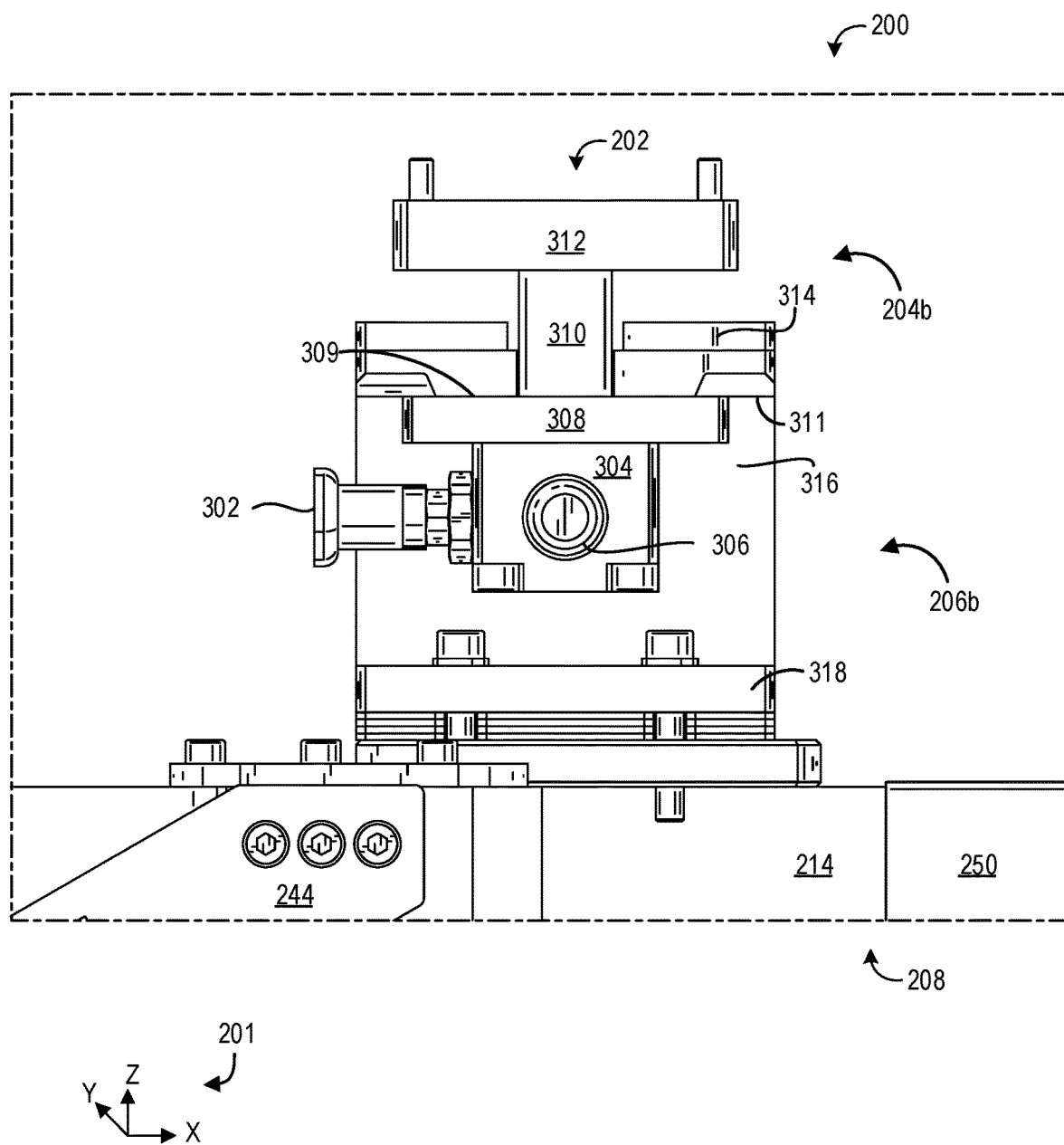
FIG. 8 shows a table interface of the patient table support, according to an embodiment of the disclosure.
Figure 9:
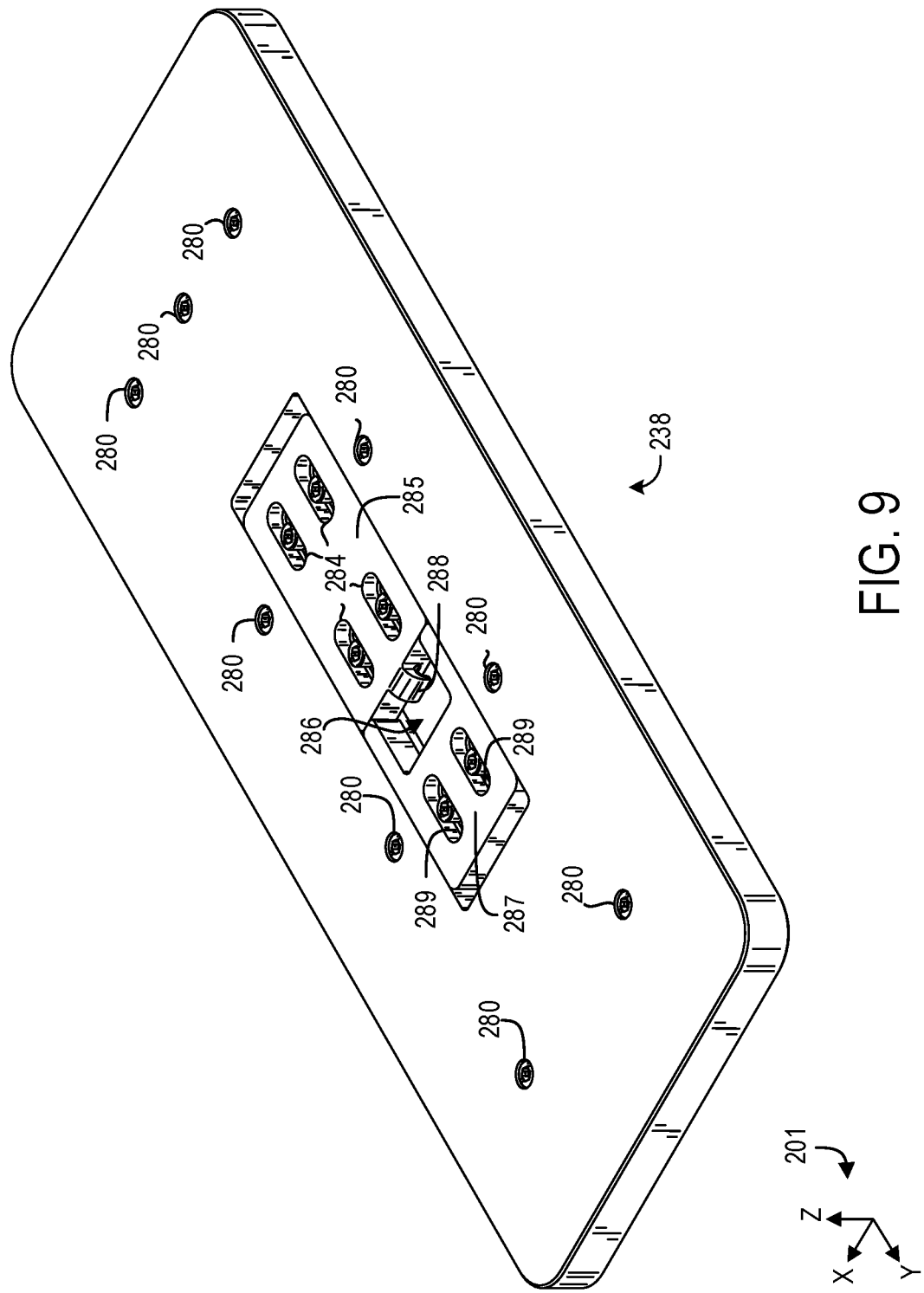
FIG. 9 shows a floor panel of the patient table support, according to an embodiment of the disclosure.
Figure 10:
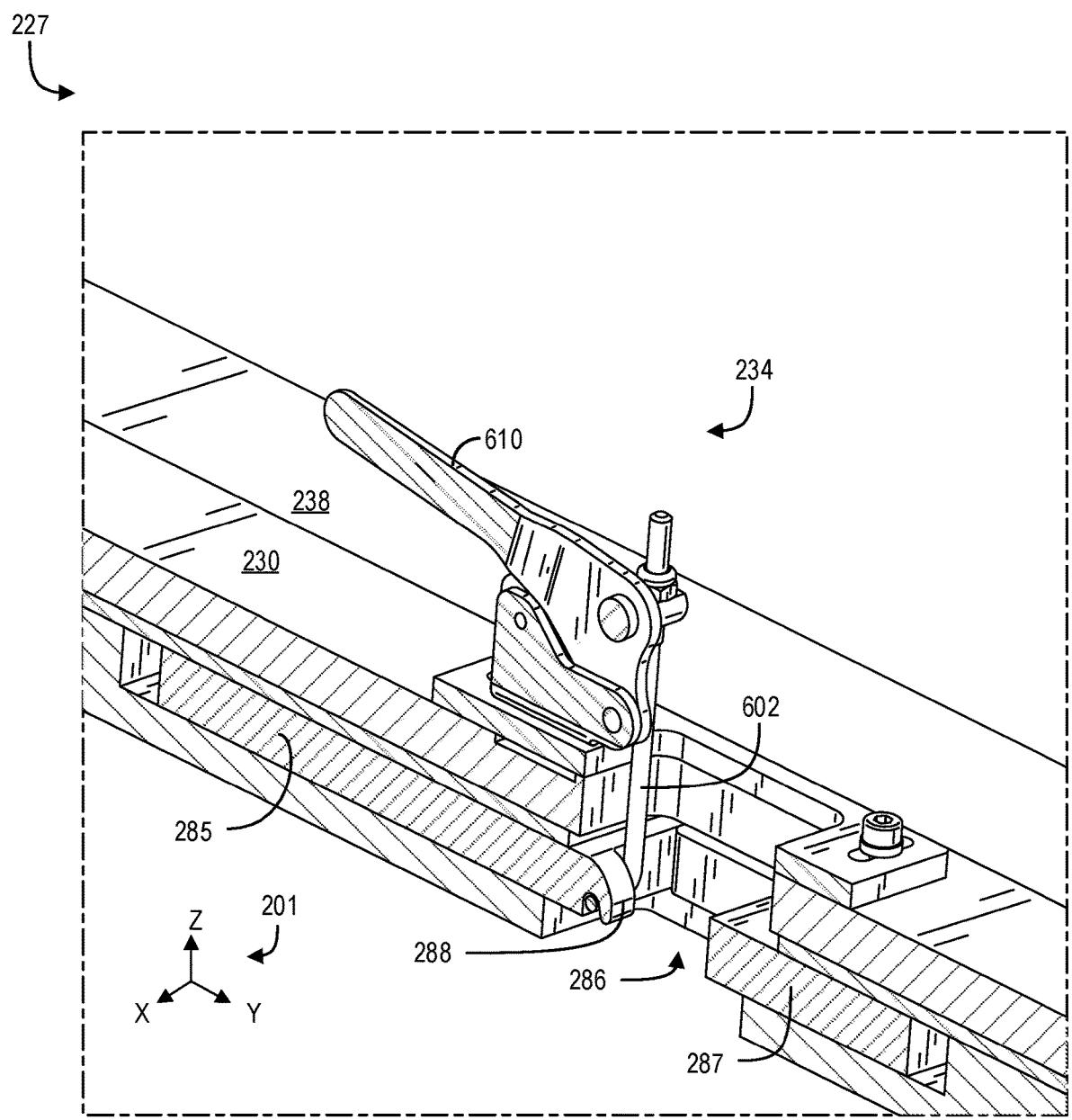
FIG. 10 shows a second cross-sectional view of the patient table support.
Figure 11:
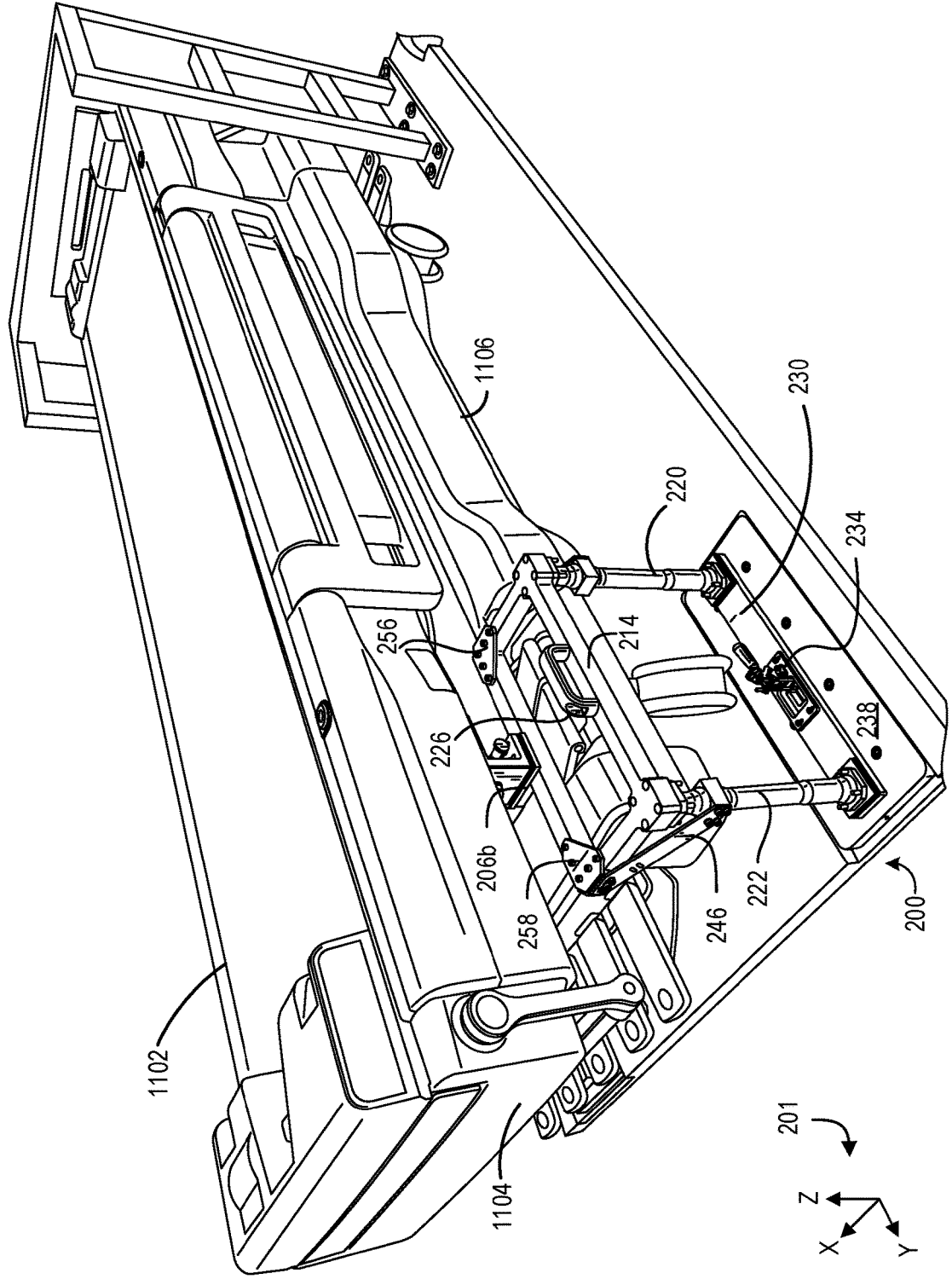
FIG. 11 shows a perspective view of the patient table support coupled to a patient table.
Figure 12:
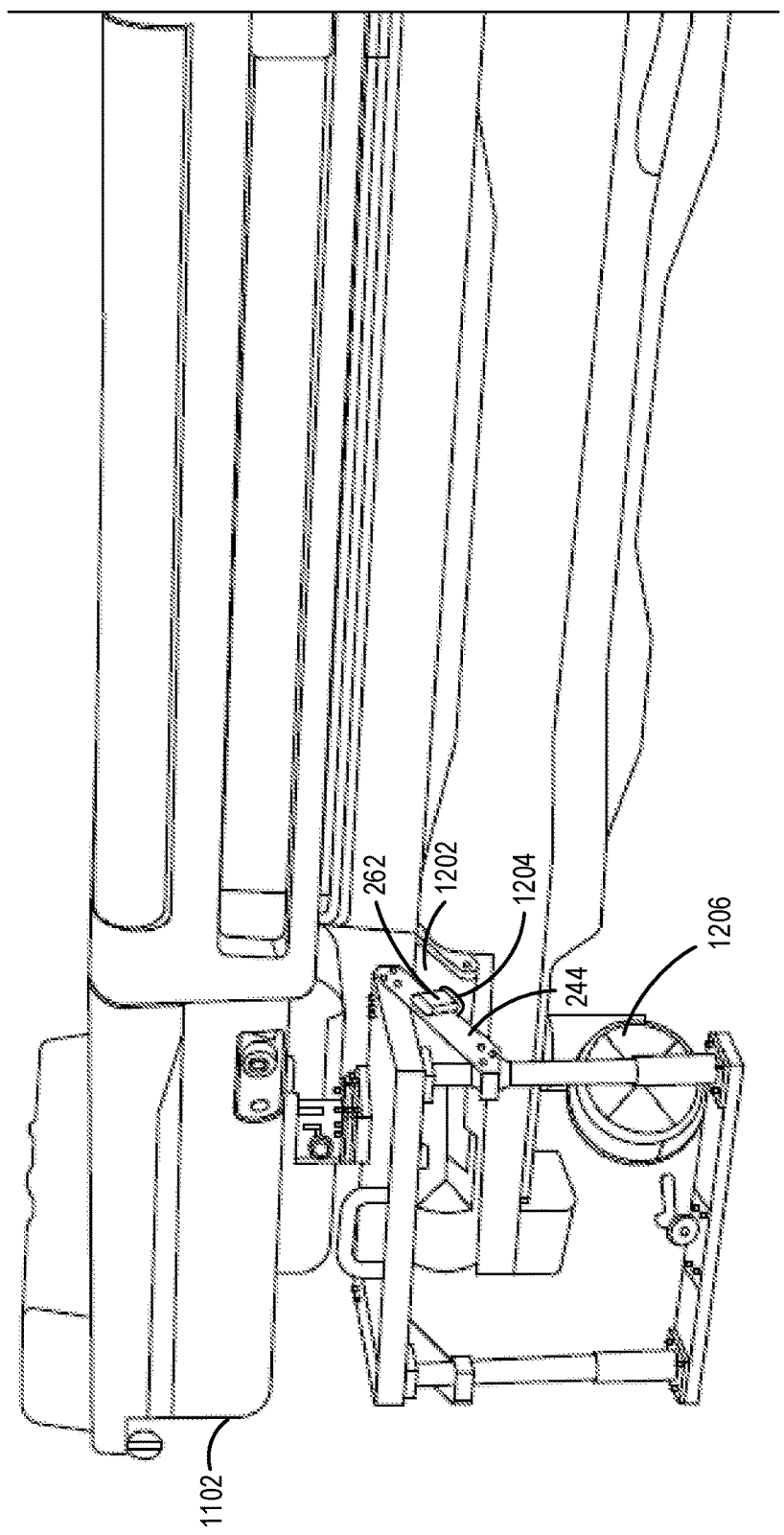
FIG. 12 shows a side view of the patient table support locked to the patient table, according to an embodiment of the disclosure.

FIGS. 2-12 show a table support 200 and/or aspects of the table support 200 and will be described collectively, with like components numbered the same throughout FIGS. 2-12. FIG. 2 and FIG. 3 are perspective views of the table support 200 from two different sides. FIG. 4 shows a first side view of the table support 200. FIG. 5 shows a top-down view of the table support 200. FIG. 6 shows a first cross-sectional view of the table support 200 taken across line A-A' of FIG. 5. FIG. 7 is a second side view of the table support 200. FIG. 8 shows a table interface of the table support 200. FIG. 9 shows a floor panel of the table support 200. FIG. 10 is a second cross-sectional view of the table support 200 taken across line B-B' of FIG. 5. FIG. 11 is a perspective view of the table support 200 coupled to a patient table. FIG. 12 is a side view of the table support 200 locked to the patient table. FIGS. 2-12 are shown approximately to scale.

The table support 200 may include a table interface 202, a fixture 208, and a floor interface 227. The table interface 202 comprises two table flanges: a first table flange 204a and a second table flange 204b, both configured to be affixed to an underside of a patient table (not shown in FIG. 2 for visual clarity) via bolts or another suitable coupling mechanism. When the table support 200 is coupled to the patient table, the first and second table flanges may be positioned into complementary table flange acceptors that may be attached to the fixture 208. The table flanges and the table flange acceptors may each be comprised of stainless steel (e.g., grade 316 stainless steel) or another suitable material.

Thus, as shown in FIGS. 2 and 3, the first table flange 204a may be positioned in a first table flange acceptor 206a and the second table flange 204b may be positioned in a second table flange acceptor 206b. Each table flange acceptor may be C-shaped, with a top portion configured to interface with the table flange, a back wall, and a bottom portion configured to be coupled to the fixture 208. For example, as shown in FIG. 3 and as will be explained in more detail below with respect to FIG. 8, the second table flange acceptor 206b includes a top portion 314, a back wall 316, and a bottom portion 318. The top portion 314 may include two layers, with a first layer having a surface that is in face-sharing contact with a surface of the second table flange 204b and a second layer that forms the top wall of the C-shape. The second layer of the top portion 314 (referred to as the top wall of the table flange acceptor) may be coupled to (or be formed integrally with) the back wall 316, which in turn may be coupled to (or be formed integrally with) a bottom wall of the bottom portion 318. The top portion 314 and the bottom portion 318 may extend outward from the back wall 316 in respective x-y planes, parallel to the y-axis (e.g., parallel to flat ground). The top portion 314 may include a Y-shaped slot within which a portion of the second table flange 204b may be accommodated. In this way, each table flange may be positioned within a respective table flange acceptor, and the C-shape of the table flange acceptor may allow for the table flange to be easily positioned within the table flange acceptor and then secured, as explained below. Further, the C-shape of the table flange acceptor may also allow the weight of the fixture 208 to be supported during the sliding motion, which may reduce the uplifting force the operator needs to provide.

The fixture 208 includes a frame comprising a first frame portion 210, a second frame portion 214 (each lying in the same x-y plane), and a cross-bracket 212 (extending along the x-axis) coupled between the first frame portion 210 and the second frame portion 214. The fixture 208 (including the posts described below) may be comprised of aluminum or an aluminum alloy (such as aluminum alloy 6061). Each of the first frame portion 210 and second frame portion 214 may be rectangularly shaped and comprised of rectangular or square members, each member having a substantially rectangular central cutout or void. The first frame portion 210 and second frame portion 214 are symmetrical to each other about the y-z plane. Thus, aspects of one of the frame portions described herein likewise applies to the other frame portion.

For example, the second frame portion 214 comprises a first side 502, a second side 504, a third side 506, and a fourth side 508. The first side 502 and third side 506 have the same length, which may be approximately double the length of second side 504 and third side 506, which are opposite each other and parallel. The first frame portion 210 likewise includes a first side, a second side, a third side, and a fourth side that form a rectangle, with the first and third sides being parallel to one another and longer than the second and fourth sides. The cross-bracket 212 is coupled to the first side 502 of the second frame portion 214 at a midpoint of the first side 502, forming a second T-junction 215. Similarly, the cross-bracket 212 is coupled to the first frame portion 210 at a midpoint of a first side of the first frame portion 210, forming a first T-junction 213.

Each of the first table flange acceptor 206a and second table flange acceptor 206b may be positioned at (and firmly coupled to) a first and second T-junction, where the cross-bracket 212 couples to the first frame portion 210 at first T-junction 213 and the second frame portion 214 at second T-junction 215, respectively. Placing the table flange acceptors directly above the T-junctions allows for the table flange acceptors to have support in both the x- and y-directions; support in the x-direction comes from the cross-bracket 212 and support in the y-direction comes from the first and second T-junctions. Furthermore, the table flange acceptors are as close to the posts as allowed by the geometry of the table, including spatial allowances for the size of the wheels of the patient table, as shown in FIG. 11 and FIG. 12. This reduces torque components parallel to the y-axis applied at the bottoms of each post, since the load from the table flange receivers is applied in the negative z direction along axes relatively close to the axes of the posts. To accommodate tables with different widths, the length of the cross-bracket 212 may be changed in various embodiments to alter the spacing between the first table flange acceptor 206a and second table flange acceptor 206b.

The fixture 208 further includes a plurality of posts coupled between the frame and the floor interface 227. The posts are coupled to the frame portions via bolts or another suitable coupling mechanism. As shown, the posts are coupled to frame portions via a set of four bolts per post. The plurality of posts includes a first post 216 and a second post 218 each coupled to the first frame portion 210 and a third post 220 and a fourth post 222, each coupled to the second frame portion 214. Further detail of the posts is described below with respect to FIG. 4. The third post 220 may be coupled to a first outer corner of the second frame portion 214 where the third side 506 and the fourth side 508 are joined. The fourth post 222 may be coupled to a second outer corner of the second frame portion 214 where the third side 506 and the second side 504 are joined. Similarly, the first post 216 is coupled to a first outer corner of the first frame portion 210 and the second post 218 is coupled to a second outer corner of the first frame portion 210. Thus, each post is coupled to a respective outer corner of a frame portion, where an outer corner may be positioned distal to a middle of the table support 200 (e.g., distal to the cross-bracket 212). Each outer corner may include additional material so that each outer corner may match a size and shape of the top of a respective post. Each frame portion may include two inner corners, each opposite a respective outer corner, positioned proximate to the middle of the table support 200 relative to the outer corners.

To provide support and stability to the inner corners of the frame portions, the table support includes a plurality of corner reinforcement plates and braces. The first frame portion 210 includes first corner reinforcement plate 252 and second corner reinforcement plate 254; second frame portion 214 includes third corner reinforcement plate 256 and fourth corner reinforcement plate 258. The first corner reinforcement plate 252 and second corner reinforcement plate 254 are affixed to the inner corners of the first frame portion 210 (e.g., nearest to the cross-bracket 212) via a series of bolts or other suitable coupling mechanism. Similarly, the third corner reinforcement plate 256 and fourth corner reinforcement plate 258 are affixed to the inner corners of the second frame portion 214 (e.g., nearest to the cross-bracket 212) via a series of bolts or other suitable coupling mechanism. Each corner reinforcement plate is affixed to the top of the fixture 208 via a set of bolts or other suitable coupling mechanism and lies in the same x-y plane. The collection of corner reinforcement plates serves to stabilize the fixture 208 by resisting torques with components in the z-axis.

The first frame portion 210 and second frame portion 214 are coupled to the each of the plurality of posts via a plurality of braces, including first brace 240 connecting first post 216 and first frame portion 210, second brace 242 connecting second post 218 and first frame portion 210, third brace 244 connecting third post 220 and second frame portion 214, and fourth brace 246 connecting fourth post 222 and second frame portion 214. The braces are configured to provide additional support to the fixture 208, especially for resistance to forces (e.g. from the weight supported by the table interface) with components in the x-z plane and torques with components along the y-axis. The third brace 244 is shown in greater detail in FIG. 7.

A first, top side of fourth brace 246 is coupled to the second side 504 of the second frame portion 214 at the inner corner between the second side 504 and the first side 502 using, in an example, three bolts arranged in a horizontal line. In other embodiments, the quantity and distribution of bolts affixing third brace 244 to the second frame portion and third post may vary. For example, if the top side of third brace 244 is wider in the x-direction, more bolts may be used to affix the top side of third brace 244 to the second frame portion 214. A second, bottom end of fourth brace 246 is further coupled to the fourth post 222, specifically at an enlarged, square-shaped coupling portion of the fourth post 222, as explained with regard to FIG. 4 and FIG. 7. In this way, fourth brace 246 is coupled to the outside of the fixture 208 to account for space required by first side 502 where it couples to the second side 504. Similarly, third brace 244 is coupled to the third post 220 and to the fourth side 508 of second frame portion 214. As explained previously, first frame portion 210, first brace 240, and second brace 242 are similar to second frame portion 214, third brace 244, and fourth brace 246, and thus first brace 240 is coupled at a first, top end to a short side of the first frame portion at one inner corner of the first frame portion and coupled at a second, bottom end to first post 216 and second brace 242 is coupled at a first, top end to a short side of the first frame portion at the other inner corner of the first frame portion and coupled at a second, bottom end to second post 218.

FIG. 3 further shows a first braking block 260 attached to first brace 240 and a second braking block 262 attached to third brace 244. The first braking block 260 and second braking block 262 both have a suitable size and shape (e.g., rectangular) that is configured such that each braking block can be positioned within a respective groove of a brake pedal of the patient table. The centers of each braking block are approximately centered within their respective braces. The first braking block 260 and second braking block 262 are configured to interlock with (and thus hold down) complementary grooves within brake pedals of the patient table, as shown in FIG. 12. Further details of the third brace 244 and the second braking block 262 are shown with respect to FIG. 7.

The fixture 208 further includes two sets of handles positioned on the frame to facilitate movement of the fixture 208 during installation and uninstallation. As shown, a set of exterior handles includes a first exterior handle 224 positioned on the first frame portion 210 and a second exterior handle 226 positioned on the second frame portion 214. The first exterior handle 224 and the second exterior handle 226 are spaced in the x-direction by a first, larger amount. The set of exterior handles is positioned on the outside of the fixture to allow for two operators or one relatively tall/large operator to lift and/or carry the fixture 208. Fixture 208 further includes a set of interior handles comprising a first interior handle 248 and a second interior handle 250 positioned on the cross-bracket 212 and spaced in the x-direction by a second, smaller amount (e.g., smaller than the amount the set of exterior handles are spaced apart) to facilitate movement of the fixture 208 by a single operator. In the embodiment described herein, the first interior handle 248 and second interior handle 250 comprise a pair of rubberized grips. Rubberized grips are used instead of raised handles (as in the first set of handles) to allow the cross-bracket 212 to fit beneath the patient table. In other embodiments, the set of internal handles may comprise a pair of raised handles, similar to the set of external handles, but lying in the x-y plane to allow for spatial clearance of the table.

The floor interface 227 includes a set of floor brackets and a set of floor panels. The set of floor brackets is included as part of the fixture 208 and the set of floor panels may be attached to the floor of the trailer through, for example, a series of bolts 270 (see FIG. 4 and FIG. 6). Coupled between each set of posts is a respective floor bracket, including a first floor bracket 228 coupled between the first post 216 and the second post 218 and a second floor bracket 230 coupled between the third post 220 and the fourth post 222. Each floor bracket includes a locking clamp, such as a first locking clamp 232 on first floor bracket 228 and a second locking clamp 234 on second floor bracket 230, that may be moved via a handle to secure or unsecure the respective floor bracket from a corresponding floor panel (e.g. first floor panel 236 and second floor panel 238). The floor panels may feature complementary internal wells to allow for the first locking clamp 232 and second locking clamp 234 to effectively couple with the first floor panel 236 and second floor panel 238. Each floor bracket, such as floor bracket 230, may have a bottom layer comprised of material configured to absorb vibrational forces, such as resilient material (e.g., a spring), rubber, foam, or another suitable material.

FIG. 4 shows the table support 200 as viewed from its right side. For visual clarity, the table interface 202 is not shown. FIG. 4 shows the mechanical coupling between the floor, the second floor panel 238, and the second floor bracket 230. It should be appreciated that the first floor panel and second floor bracket are identical to the second floor panel 238 and second floor bracket 230, except that they are coupled to the first and second posts instead of the third post 220 and fourth post 222. Further internal detail of the second locking clamp 234 and the internal coupling between the second floor bracket 230 and second floor panel 238 is shown in FIG. 7.

In addition, FIG. 4 also shows the components of third post 220 in more detail. It should be appreciated that first post 216, second post 218, and fourth post 222 are identical to third post 220. Third post 220 includes (in vertical order from bottom to top) a first post portion 402, a second post portion 404, a third post portion 406, a fourth post portion 408, and a fifth post portion 410. The first post portion 402 is closest to the ground, having a substantially square shape and several holes in the z-direction to allow for bolts or another sufficient coupling mechanism to affix the post to its respective floor bracket. The first post portion 402 may be a coupling flange shaped and sized to couple the third post to the floor bracket and may have a first width W1. The second post portion 404 has a circular cross-section with a diameter D1 that is smaller than the width W1 of first post portion 402. Further, at the bottom of the second post portion 404 where the second post portion 404 transitions to the first post portion 402, the diameter of the second post portion may gradually increase. The third post portion 406 has a circular cross-section with a diameter D2 that is smaller than the diameter D1 of the second post portion 404. The fourth post portion 408, which couples to third brace 244 and thus is an example of the square-shaped coupling portion described above, is rectangular with a width W2 approximately equal to the width of first post portion 402. Fourth post portion 408 is coupled with third brace 244, allowing for additional structural reinforcement of the fixture 208 in the x-z plane. The fifth post portion 410 is circular and has a diameter D3 that, at the narrowest section of the fifth post portion 410, may be equal to the diameter D2 of the third post portion 406. Fifth post portion 410 further includes a substantially rectangular sixth portion 412 on its top, allowing for third post 220 to mechanically couple to second frame portion 214 (e.g. through the use of bolts). The second post portion 404 of the post is wider than other portions of the post in order to resist cracking of the post closest to the floor bracket. The lowest portions of the post are designed to resist torques about the coupling between the floor bracket and the post due to loads, such as loads from the table interface or loads from the weight of the fixture 208. Further, each post may have a hollow interior of constant diameter along an entire length of the post, such that the portions of the posts described herein that have increased width (e.g., the second post portion 404) relative to other portions of the posts may have increased material surrounding the hollow interior at those portions. Further still, while circular posts are shown and described, it should be appreciated that the posts may have other shapes without departing from the scope of this disclosure, such as rectangular.

In regions of the third post 220 that change in diameter or width, the post may taper inward or outward in a gradual manner. For example, the third post portion 406 may taper inward from the second post portion 404 at a suitable angle (e.g., 80° relative to the y axis) and may taper outward to the fourth post portion 408 at another angle (e.g., 110° relative to the y axis). The fifth post portion 410 be substantially tapered, such that the fifth post portion 410 tapers inward and then outward with only a small intervening straight portion (e.g., less than 50% of the total length of the fifth post portion 410). The third post portion 406 may be the longest portion of the third post 220, with a length that is greater than a length of the second post portion 404, such as twice as long as the second post portion 404. The fourth post portion 408 may have a length sized to accommodate the coupling of third brace 244. Further, the third post 220 may be coupled to second floor bracket 230 via a coupling member 701, which may further act to absorb forces and reduce vibrations.

FIG. 5 shows a top-down perspective of the table support 200. As appreciated in the top-down view, the sides of each frame portion do not all have equal widths. Rather, each first side (e.g., first side 502) may be wider along the x-axis than each third side (e.g., third side 506. Each second side, third side, and fourth side may have the same width. The increased width of each first side may allow each frame portion to better withstand the load placed on the fixture by the table. As also appreciated in the top-down view, the table flange acceptors may extend with a length along the y-axis that is longer than a width of the table flanges along the y-axis. For example, the top portion 314 may have a length along the y-axis that is at least twice as long as a width of upper part 312 along the y-axis.

Additionally, FIG. 5 includes two cut planes: the plane specified by the line from A to A' and the plane specified by the line from B to B'. Objects within the A-A' cut plane and the B-B' cut plane are shown in greater detail with respect to FIG. 6 and FIG. 10, respectively. As appreciated in FIG. 6, the cross-bracket 212 may be substantially hollow, other than a cross-beam at a mid-point of the cross-bracket 212, which may reduce a weight of the fixture 208. In other embodiments, the cross-beam may be cylindrical instead of rectangular, and may or may not include a hollow void inside.

FIG. 7 shows additional detail of the second frame portion 214 and its coupling to third post 220. Coupled between the fourth post portion 408 of the third post 220 and the second frame portion 214 is the third brace 244. Third brace 244 may extend from the fourth post portion 408 to the second frame portion 214 at an angle 414 of approximately 30 degrees, which may enable optimal distribution of the forces acting on the portions of the frame (e.g., the inner corners) that are otherwise unsupported to the posts. By configuring the fixture 208 with only four posts and with each frame portion having a void, the fixture may be made sufficiently lightweight to enable a single operator to move the table support 200 into position under a patient table, while also providing clearance for the structure of the patient table.

FIG. 8 shows further detail of the second table flange 204b and second table flange acceptor 206b, which are also shown in cross-section in FIG. 6. It should be appreciated that first table flange 204a and first table flange acceptor 206a are identical to the second table flange 204b and the second table flange acceptor 206b, respectively, and thus description of the second table flange 204b and the second table flange acceptor 206b likewise apply to the first table flange 204a and the first table flange acceptor 206a. The second table flange 204b comprises an upper flange part 312, a middle flange part 310 (with a width of approximately 25% of the width of the upper part), a lower flange part 308 (with a width approximately equal to the upper part 312), and a shaft receiver 304. The middle flange part 310 comprises a shaft extending in the vertical direction (e.g., along the z-axis) that is configured to fit into a Y-shaped slot within the top portion 314 of the second table flange acceptor 206b (e.g., within the top wall of the second table flange acceptor 206b), and thus may also be referred to as a vertical shaft. When the table support is coupled to the table such that the table flanges are positioned within the table flange acceptors, an upper surface 309 of lower flange part 308 is in face-sharing contact with a lower surface 311 of the top portion 314 (e.g., with a lower surface of the top wall of the second table flange acceptor 206b). The middle flange part 310 fits directly into the center of the stem of the Y-shaped slot, but is very slightly narrower than the stem of Y-shaped slot, allowing for a mechanical tolerance when coupling the table flange acceptor to the table flange. The Y-shaped slot may be defined by the top portion 314, which may have a triangular cutout that joins with a straight cutout, thereby forming the Y-shape. The triangular portion of the Y-shaped slot may be wider at the distal edge of the top portion 314 (opposite from and distal to the back wall 316) and may narrow in a direction toward the back wall 316. For example, the opening of the top portion 314 at the distal edge may have a width of approximately 70% of the width of the top portion 314, linearly narrowing to approximately 20-30% of the width of the width of the top portion 314 at the stem. In this way, when the fixture 208 is positioned under the patient table, the fixture 208 may be positioned so that the middle part 310 is first accommodated within the wider portion of the Y-shaped slot and then the fixture 208 may be moved until the middle part 310 is positioned at the back of the stem of the Y-shaped slot, with constraints provided by the narrowing of the triangular portion of the Y-shaped slot.

The second table flange 204b further includes the shaft receiver 304, which is configured to receive a complementary locking shaft 306 extending from the center of the second table flange acceptor 206b. The locking shaft 306 also has a hole along the x-axis to receive a locking thumbscrew 302 of the second table flange 204b to secure the second table flange 204b to the second table flange acceptor 206b. For example, to secure the second table flange 204b to the second table flange acceptor 206b, an operator may positon the second table flange 204b within the second table flange acceptor 206b such that the vertical shaft/middle flange part is seated within the stem of the Y-shaped opening and the locking shaft 306 is seated within the shaft receiver 304, and then the operator may actuate (e.g., turn) the thumbscrew 302 to secure the locking shaft 306 in position. In other examples, rather than a thumbscrew, the table flanges may include spring-loaded locking pins or another suitable locking mechanism.

The second table flange acceptor 206b is mechanically coupled to the fixture 208 at the bottom portion 318 through bolts or another sufficient coupling mechanism. The bottom portion 318 may include multiple layers, including a first layer that forms part of the C-shape of the flange acceptor, a coupling layer that is in face-sharing contact with the fixture, and an intermediate layer between the first layer and the coupling layer. The intermediate layer may be comprised of material configured to absorb vibrational forces, such as resilient material (e.g., a spring), foam, or another suitable material.

As appreciated from FIG. 8, the table flanges do not rest on top of any surfaces of the table flange acceptors. Rather, the table flange acceptors rest on a surface of the table flanges (e.g., upper surface 309). When the fixture is secured to the floor panels via the clamps in the floor brackets, the table flange acceptors provide a downward force on the table flanges, restricting upward movement of the patient table in the vertical direction (e.g., in the positive z direction), while the locking of the locking shaft 306 to the shaft receiver 304 restricts downward movement of the patient table in the vertical direction (e.g., in the negative z direction). The friction between the face-sharing contact surfaces of the table flanges and table flange acceptors as well as the locking of the locking shaft 306 to the shaft receiver 304 restricts lateral movement of the patient table in the horizontal direction (e.g., along the x-axis).

FIG. 9 shows additional detail of the second floor panel 238 (the first floor panel 236 is identical, as explained above with respect to FIG. 4). In the embodiment shown, second floor panel 238 features a series of nine holes 280 drilled in a rectangular pattern. The holes allow the floor panel to be bolted (e.g. with a series of bolts 270, as described with respect to FIG. 4 above) to the floor of a transportation unit, such as a trailer. It should be noted that the quantity, arrangement, and diameter of the holes 280 may differ in various embodiments. For example, different hole patterns may be used in different embodiments in order to fit the floors of different truck beds.

Furthermore, the length, width, and thickness of second floor panel 238 may be varied depending on the desired use case. A wider and/or longer second floor panel 238 would increase a surface area of the second floor panel 238, allowing for loads to be more evenly distributed along the floor it is attached to. On the other hand, a smaller length and/or width may reduce the weight of second floor panel 238.

The second floor panel 238 further includes a substantially rectangular cutout or void to accommodate two movable components: hook block 285 and receiving well block 287; each is coupled to second floor panel 238 via a respective set of bolts. Hook block 285 includes an integrated inverted circular hook 288 designed to removably couple to an element of second locking clamp 234. The hook block 285 is affixed to the second floor panel 238 through four bolts, each threaded through one of a series of slots 284 milled into the hook block 285. The slots 284 are milled in the y-direction, allowing for the hook block 285 to be moved in the y-direction with respect to the second floor panel 238. This is advantageous since the position of the inverted circular hook 288 may be adjusted beforehand as a manufacturing procedure and then secured, so that the operator does not have to precisely align the fixture with the floor (which may take an extensive amount of time, and thus the configuration described herein may result in a rapid locking procedure). The receiving well block 287 is similarly coupled to the second floor panel 238 through two slots 289 milled in the y-direction. The slots 289 allow for the receiving well block 287 to be slid forwards and backwards, maintaining the dimension of the internal receiving well 286 to ensure the hole on the floor does not present a risk of tripping. The internal receiving well 286 (e.g. a rectangular void) and the inverted circular hook 288 allow for removable coupling via the second locking clamp 234, as explained further with respect to FIG. 10.

FIG. 10 shows a cross-sectional view (along line B-B' of FIG. 5) of the coupling between the second floor panel 238 and second floor bracket 230, according to an embodiment. The second floor bracket 230 and second floor panel 238 are shown removably coupled via the second locking clamp 234. It should be noted that second locking clamp 234 comprises one possible embodiment of a floor clamp. Other locking clamp mechanisms may be used instead to removably couple the floor panel and floor bracket. As explained above, second floor panel 238 includes the internal receiving well 286, which is a substantially rectangular cutout or void, allowing room for the clamp to attach to an inverted circular hook 288 within the internal receiving well 286. In some embodiments, inverted circular hook 288 may instead be substantially rectangular. The second floor bracket 230 likewise includes an internal well that, when the fixture 208 is positioned over the floor panels such that the second floor bracket 230 is positioned above the second floor panel 238, aligns with the internal receiving well 286 to create a shared opening through which aspects of the second locking clamp 234 may be accommodated.

While any suitable locking clamp may be used, FIG. 10 illustrates one example of the second locking clamp 234, which may include a handle for the clamp to engage a lip or other feature of the second floor bracket or second floor panel to lock the second floor bracket to the second floor panel via the locking clamp. In some examples, a post 602 of the second locking clamp 234 may couple to the inverted circular hook 288. The post 602 may be moved via an exterior handle 610 operated by the user. When locked, the post 602 may extend through the internal well of the second floor bracket 230 and into the internal receiving well 286 of the second floor panel 238. The post 602 may include a curved region at the bottom end of the post 602 that is positioned under/within the inverted circular hook 288. When the second floor bracket is locked to the second floor panel via the locking clamp, the exterior handle 610 may be manipulated so that post 602 may be positioned under the inverted circular hook 288, and the exterior handle 610 may be moved (e.g., downward) to secure the curved region of the post 602 within the inverted circular hook 288 and a locking mechanism may be actuated to maintain the post 602 in position. A reverse operation may be performed to unlock the second locking clamp 234. It should be appreciated that second locking clamp 234 is exemplary and other mechanisms of securing the floor bracket to the floor panel are within the scope of this disclosure.

FIG. 11 shows the table support 200 coupled to a patient table 1102 via the table interface 202 and coupled to the floor via the floor interface 227. The patient table 1102 shown in FIG. 11 is a non-limiting example of table 26 and is shown in a lowered position.

The patient table 1102 may be secured for transport through the use of the table interface 202, the fixture 208, and floor interface 227. The first table flange 204a and second table flange 204b may be fixed to the bottom of the patient table 1102 during manufacture (or retrofitted at some later point) at positions aligned with the respective positions of the first table flange acceptor 206a and second table flange acceptor 206b. The table flanges generally do not need to be removed outside of transportation, and may be installed as permanent fixtures of the table. To ready the table for transportation, a fitting sequence may be taken to attach the patient table 1102 to the floor via the fixture. The table may be lifted while the table is still attached to the imaging system (e.g., the bore of the MRI system), such that the table may only move vertically, with limited lateral movement. The fixture 208 may be slid beneath the patient table 1102, allowing the first table flange acceptor 206a and second table flange acceptor 206b to accept the first table flange 204a and second table flange 204b and couple the table to the fixture 208. With the fixture 208 attached, the patient table 1102 may be lowered such that the floor brackets make contact with the floor panels (e.g., such that second floor bracket 230 is positioned on second floor panel 238). After aligning the first locking clamp 232 and the second locking clamp 234 with respective floor panels, each locking clamp may be tightened using its respective handle (e.g. exterior handle 610), affixing the floor brackets (and therefore the table) to the floor.

As shown in FIG. 11, the patient table 1102 may include two sections that are coupled via a lifting mechanism. The two sections may include a top section 1104 and a bottom section 1106. The lifting mechanism (not visible in FIG. 11) may be configured to move the top section 1104 up and down relative to the bottom section 1106, which may have a fixed vertical position. The lifting mechanism may be positioned at a midpoint of the patient table 1102 along the y-axis and may not extend along an entire length of the top section 1104 or the bottom section 1106. As such, the first and second table flanges may be positioned toward a bottom end of the patient table 1102, spaced away from the lifting mechanism, which may allow the table flanges to be positioned under the top section 1104. Each frame portion (e.g., second frame portion 214) may extend outward from the patient table 1102 on respective sides of the patient table 1102 along the x-axis, while the cross-bracket 212 may extend along an underside of the top section 1104. The frame portions and the posts being coupled to the outer corners of the frame portions allows for the fixture 208 to extend along the sides of the bottom section 1106, which may have a width along the x-axis that is wider than the distance between the first and second table flanges.

The fixture 208 may be relatively small compared to the patient table 1102, which may allow one operator to move the fixture 208 into/out of position. For example, the long sides of the frame portions (e.g., first side 502) may have a length along the y-axis that is in a range of 10-33% of a total length of the patient table 1102. The cross-bracket 212 may have a length along the x-axis that is approximately equal to a width of the patient table 1102 along the x-axis. The short sides of the frame portion (e.g., second side 504) may extend out from the cross-bracket with a length that is 30-50% of the length of the cross-bracket. The posts may have a height that allows the table to be secured in its non-lifted position. For example, each post may have a height along the z-axis that is 50-75% of the length of the long sides of the frame portions.

As the fixture 208 is lowered to the ground, first braking block 260 and second braking block 262 may be seated in the respective brake pedals of the patient table 1102. For example, as shown in FIG. 12, a brake pedal 1202 of the patient table 1102 may include a groove 1204. The second braking block 262 may be positioned within the groove 1204, which may act to maintain the brake pedal 1202 in a depressed position, thereby locking one or more wheels of the patient table 1102 (e.g., wheel 1206).

The first and second table flanges may also be relatively small relative to the patient table 1102, which may allow the table flanges to remain fixed to the patient table 1102 during operation (including during imaging, as the table flanges may remain outside the bore of the MRI system). For example, the upper part 312 may have a length along the x-axis that is 10-20% of the length of the cross-bracket 212 and a height of each table flange (e.g., from a top surface of the upper part 312 to a bottom surface of the shaft receiver 304) may be in a range of 15-30% of a height of each post (along the z-axis).

Thus, the table support 200 may be coupled to the patient table 1102 by moving the patient table 1102 into a first (e.g., raised) position and positioning the first table flange 204a (fixed to the patient table 1102) within the first table flange acceptor 206a of the table support 200 and positioning the second table flange 204b (fixed to patient table 1102) within the second table flange acceptor 206b of the table support 200. For example, the table support 200 may be lifted (e.g., via the external or internal handles) and then moved laterally until the vertical shaft of the first table flange 204a is positioned within the Y-shaped opening (e.g., within the stem of the Y-shaped opening) of the top wall of the first table flange acceptor 206a, and the vertical shaft 310 of the second table flange 204b is positioned within the Y-shaped opening (e.g., within the stem of the Y-shaped opening) of the top wall 314 of the second table flange acceptor 206b. The locking shaft (e.g., shaft 306) of each table flange acceptor may be positioned within a respective shaft receiver (e.g., shaft receiver 304) and secured via a thumbscrew/locking pin of the table flange (e.g., thumbscrew 302). Each vertical shaft of each table flange may be coupled between a respective top flange part (e.g., top part 312) and a respective bottom flange part (e.g., bottom part 308). Each top flange part may be coupled to the patient table and each bottom flange part may have a planar surface (e.g., upper surface 309) configured to be in face-sharing contact with a lower surface of the table flange acceptor (e.g., lower surface 311).

Once the table support 200 is secured to the table 1102 via the flanges/flange acceptors, the patient table 1102 may be lowered to a second position (which may be vertically lower than the first position) where the bottom of the floor brackets of the table support may contact the top of the floor panels, and each locking clamp (e.g., locking clamp 234) of the table support may be locked to a respective floor panel (e.g., floor panel 238) by actuating the handle of the floor clamp so that a post of the locking clamp is held within a hook of the floor panel.

In this way, the table support 200 may be secured to the patient table 1102 while the patient table 1102 is lifted and then the patient table 1102 may be lowered so that the table support 200 may be secured to the floor. By doing so, the coupling of the table support to the patient table may be easier for an operator to perform, as the operator may be able to better see and feel for the proper interfacing between the table flanges and table flange acceptors. Further, the lightweight nature of the table support (e.g., owing to the hollow portions of the frame) and positioning of the two sets of handles may allow a diversity of operators to easily lift and secure the table support to the table, without compromising the stability provided by the table support. The use of the thumbscrews/locking pins and locking clamps may avoid the need to rely on loose screws or bolts to secure the table support to the table and/or floor, which may make installation and removal of the table support easy and reduce the need to secure or replace loose hardware. Furthermore, the table flanges may be fixed to a bottom end of the patient table and the top end of the patient table may be supported by the mobile imaging system (e.g., the bore of the MRI system) when the table support is initially coupled to the patient table and when the patient table is lowered to the second position, as well as when the table support is coupled to the floor. This may reduce or eliminate the need to ensure the floor is level during installation of the table support.

The disclosure also provides support for a table support for a mobile imaging system, comprising: a fixture comprising a frame and a plurality of posts coupled to the frame, a table interface comprising a set of table flanges configured to be attached to a patient table of the mobile imaging system and a set of complementary table flange acceptors coupled to a top surface of the frame of the fixture, and a floor interface including a set of floor brackets removably coupleable to a set of floor panels configured to be attached to a floor of a unit configured to house the mobile imaging system, each floor bracket coupled to two respective posts of the plurality of posts. In a first example of the table support, the frame comprises a first frame portion, a second frame portion, and a cross-bracket coupled between the first frame portion and the second frame portion, where each of the first frame portion and the second frame portion is rectangular, with a first long side of the first frame portion coupled to the cross-bracket at a first T-junction and a first long side of the second frame portion coupled to the cross-bracket at a second T-junction. In a second example of the table support, optionally including the first example, the complementary table flange acceptors comprise a first table flange acceptor and a second table flange acceptor, the first table flange acceptor coupled to the top surface at the first T-junction and the second table flange acceptor coupled to the top surface at the second T-junction. In a third example of the table support, optionally including one or both of the first and second examples, the plurality of posts includes a first post coupled to a first outer corner of the first frame portion and a second post coupled to a second outer corner of the first frame portion, the first outer corner formed where a second long side of the first frame portion meets a first short side of the first frame portion and the second outer corner formed where the second long side of the first frame portion meets a second short side of the first frame portion, the set of floor brackets including a first floor bracket coupled to the first post and the second post. In a fourth example of the table support, optionally including one or more or each of the first through third examples, the first frame portion includes a first inner corner and a second inner corner, the first inner corner formed where the first long side of the first frame portion meets the first short side of the first frame portion and the second inner corner formed where the first long side of the first frame portion meets the second short side of the first frame portion, and further comprising a first brace coupled to the first short side at the first inner corner and to the first post and a second brace coupled to the second short side at the second inner corner and to the second post. In a fifth example of the table support, optionally including one or more or each of the first through fourth examples, the table support further comprises: a braking block coupled to the first brace, the braking block sized and shaped to fit within a groove of a brake pedal of the patient table. In a sixth example of the table support, optionally including one or more or each of the first through fifth examples, the table support further comprises: a first set of handles and a second set of handles, a first handle of the first set of handles positioned on the first frame portion and a second handle of the first set of handles positioned on the second frame portion, the second set of handles positioned on the cross-bracket. In a seventh example of the table support, optionally including one or more or each of the first through sixth examples, each table flange acceptor comprises a top wall, a back wall including a locking shaft extending therefrom, and a bottom wall, where the top wall, back wall, and bottom wall collectively form a C-shape, and where the top wall includes a Y-shaped opening. In an eighth example of the table support, optionally including one or more or each of the first through seventh examples, the Y-shaped opening is configured to receive a coupling portion of a respective table flange, and wherein the locking shaft is configured to be positioned within a shaft receiver of the respective table flange. In a ninth example of the table support, optionally including one or more or each of the first through eighth examples, each floor bracket includes a locking clamp configured to removably couple that floor bracket to a respective floor panel.

The disclosure also provides support for a table support for a mobile imaging system, comprising: a frame comprising a first frame portion, a second frame portion, and a cross-bracket coupled between the first frame portion and the second frame portion, each of the first frame portion and the second frame portion being rectangular shaped and having a central void, a plurality of posts, each post coupled to a respective outer corner the frame, a first table flange acceptor coupled to the frame at a first T-junction where the cross-bracket couples to the first frame portion and a second table flange acceptor coupled to the frame at a second T-junction where the cross-bracket couples to the second frame portion, each table flange acceptor forming a C-shaped opening configured to accommodate a respective table flange attached to a patient table of the mobile imaging system, and a set of floor brackets removably coupleable to a set of floor panels attached to a floor of a transport unit configured to house the mobile imaging system, each floor bracket coupled to two respective posts of the plurality of posts. In a first example of the table support, each table flange acceptor includes a top wall that forms a top of the C-shaped opening, each top wall having a Y-shaped opening configured to accommodate a vertical shaft of a respective table flange, and wherein each table flange acceptor includes a back wall that forms part of the C-shaped opening, each back wall including a locking shaft configured to be secured within a respective table flange. In a second example of the table support, optionally including the first example, each top wall includes a lower surface configured to be in face-sharing contact with an upper surface of a respective table flange when the table support is coupled to the patient table. In a third example of the table support, optionally including one or both of the first and second examples, the table support further comprises: an external set of handles and an internal set of handles, a first handle of the external set of handles positioned on the first frame portion and a second handle of the external set of handles positioned on the second frame portion, the internal set of handles positioned on the cross-bracket. In a fourth example of the table support, optionally including one or more or each of the first through third examples, the table support further comprises: a set of braces, each brace coupled to a respective inner corner of the frame and to a respective post of the plurality of posts.

The disclosure also provides support for a method for securing a patient table of a mobile imaging system, comprising: with the patient table in a first position, coupling a table support to the patient table by positioning a first table flange of the patient table within a first table flange acceptor of the table support and positioning a second table flange of the patient table within a second table flange acceptor of the table support, the first table flange acceptor and the second table flange acceptor positioned on a top surface of a frame of the table support, lowering the patient table to a second position and locking a first locking clamp of the table support to a first floor panel and locking a second locking clamp of the table support to a second floor panel, the first locking clamp positioned on a first floor bracket of the table support, the first floor bracket coupled to a first set of posts of the table support, the second locking clamp positioned on a second floor bracket of the table support, the second floor bracket coupled to a second set of posts of the table support. In a first example of the method, positioning the first table flange within the first table flange acceptor comprises positioning a first vertical shaft of the first table flange within a first Y-shaped opening of a first top wall of the first table flange acceptor, the first vertical shaft coupled to a first lower flange part of the first table flange, the first lower flange part having a first upper surface that is in face-sharing contact with a first lower surface of the first top wall of the first table flange acceptor. In a second example of the method, optionally including the first example, positioning the second table flange within the second table flange acceptor comprises positioning a second vertical shaft of the second table flange within a second Y-shaped opening of a second top wall of the second table flange acceptor, the second vertical shaft coupled to a second lower flange part of the second table flange, the second lower flange part having a second upper surface that is in face-sharing contact with a second lower surface of the second top wall of the second table flange acceptor. In a third example of the method, optionally including one or both of the first and second examples, the first table flange and the second table flange are positioned at a bottom end of the patient table and a top end of the patient table is supported by the mobile imaging system when the table support is coupled to the patient table and when the patient table is lowered to the second position. In a fourth example of the method, optionally including one or more or each of the first through third examples, the method further comprises: locking one or more wheels of the patient table by positioning a braking block of the table support within a groove of a brake pedal of the patient table.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A table support for a mobile imaging system, comprising:
    a fixture comprising a frame and a plurality of posts coupled to the frame, the frame comprising a first frame portion, a second frame portion, and a cross-bracket coupled between the first frame portion and the second frame portion, and the plurality of posts including a first post coupled to a first outer corner of the first frame portion and a second post coupled to a second outer corner of the first frame portion;
    a table interface comprising a set of table flanges configured to be attached to a patient table of the mobile imaging system and a set of complementary table flange acceptors coupled to a top surface of the frame of the fixture; and
    a floor interface including a set of floor brackets removably coupleable to a set of floor panels configured to be attached to a floor of a unit configured to house the mobile imaging system, each floor bracket coupled to two respective posts of the plurality of posts, the set of floor brackets including a first floor bracket coupled to the first post and the second post.

2. The table support of claim 1, wherein each of the first frame portion and the second frame portion is rectangular, with a first long side of the first frame portion coupled to the cross-bracket at a first T-junction and a first long side of the second frame portion coupled to the cross-bracket at a second T-junction.

3. The table support of claim 2, wherein the complementary table flange acceptors comprise a first table flange acceptor and a second table flange acceptor, the first table flange acceptor coupled to the top surface at the first T-junction and the second table flange acceptor coupled to the top surface at the second T-junction.

4. The table support of claim 2, wherein the first outer corner is formed where a second long side of the first frame portion meets a first short side of the first frame portion and the second outer corner is formed where the second long side of the first frame portion meets a second short side of the first frame portion.

5. The table support of claim 4, wherein the first frame portion includes a first inner corner and a second inner corner, the first inner corner formed where the first long side of the first frame portion meets the first short side of the first frame portion and the second inner corner formed where the first long side of the first frame portion meets the second short side of the first frame portion, and further comprising a first brace coupled to the first short side at the first inner corner and to the first post and a second brace coupled to the second short side at the second inner corner and to the second post.

6. The table support of claim 5, further comprising a braking block coupled to the first brace, the braking block sized and shaped to fit within a groove of a brake pedal of the patient table.

7. The table support of claim 2, further comprising a first set of handles and a second set of handles, a first handle of the first set of handles positioned on the first frame portion and a second handle of the first set of handles positioned on the second frame portion, the second set of handles positioned on the cross-bracket.

8. The table support of claim 1, wherein each table flange acceptor comprises a top wall, a back wall including a locking shaft extending therefrom, and a bottom wall, where the top wall, back wall, and bottom wall collectively form a C-shape, and where the top wall includes a Y-shaped opening.

9. The table support of claim 8, wherein the Y-shaped opening is configured to receive a coupling portion of a respective table flange, and wherein the locking shaft is configured to be positioned within a shaft receiver of the respective table flange.

10. The table support of claim 1, wherein each floor bracket includes a locking clamp configured to removably couple that floor bracket to a respective floor panel.

11. A table support for a mobile imaging system, comprising:
a frame comprising a first frame portion, a second frame portion, and a cross-bracket coupled between the first frame portion and the second frame portion, each of the first frame portion and the second frame portion being rectangular shaped and having a central void;
a plurality of posts, each post coupled to a respective outer corner the frame;
a first table flange acceptor coupled to the frame at a first T-junction where the cross-bracket couples to the first frame portion and a second table flange acceptor coupled to the frame at a second T-junction where the cross-bracket couples to the second frame portion, each table flange acceptor forming a C-shaped opening configured to accommodate a respective table flange attached to a patient table of the mobile imaging system; and
a set of floor brackets removably coupleable to a set of floor panels attached to a floor of a transport unit configured to house the mobile imaging system, each floor bracket coupled to two respective posts of the plurality of posts.

12. The table support of claim 11, wherein each table flange acceptor includes a top wall that forms a top of the C-shaped opening, each top wall having a Y-shaped opening configured to accommodate a vertical shaft of a respective table flange, and wherein each table flange acceptor includes a back wall that forms part of the C-shaped opening, each back wall including a locking shaft configured to be secured within a respective table flange.

13. The table support of claim 12, wherein each top wall includes a lower surface configured to be in face-sharing contact with an upper surface of a respective table flange when the table support is coupled to the patient table.

14. The table support of claim 11, further comprising an external set of handles and an internal set of handles, a first handle of the external set of handles positioned on the first frame portion and a second handle of the external set of handles positioned on the second frame portion, the internal set of handles positioned on the cross-bracket.

15. The table support of claim 11, further comprising a set of braces, each brace coupled to a respective inner corner of the frame and to a respective post of the plurality of posts.

16. A method for securing a patient table of a mobile imaging system, comprising:
with a top end of the patient table coupled to a bore of the mobile imaging system and the patient table in a first vertical position, coupling a table support to a bottom end of the patient table by positioning a first table flange of the patient table within a first table flange acceptor of the table support and positioning a second table flange of the patient table within a second table flange acceptor of the table support, the first table flange acceptor and the second table flange acceptor positioned on a top surface of a frame of the table support and the table support coupled to the patient table such that a cross-bracket of the frame extends under the patient table;
lowering the patient table to a second vertical position while the table support is coupled to the patient table to bring a first floor bracket of the table support into contact with a first floor panel and a second floor bracket of the table support into contact with a second floor panel; and
locking a first locking clamp of the table support to the first floor panel and locking a second locking clamp of the table support to the second floor panel, the first locking clamp positioned on the first floor bracket of the table support, the first floor bracket coupled to a first set of posts of the table support, the second locking clamp positioned on the second floor bracket of the table support, the second floor bracket coupled to a second set of posts of the table support.

17. The method of claim 16, wherein positioning the first table flange within the first table flange acceptor comprises positioning a first vertical shaft of the first table flange within a first Y-shaped opening of a first top wall of the first table flange acceptor, the first vertical shaft coupled to a first lower flange part of the first table flange, the first lower flange part having a first upper surface that is in face-sharing contact with a first lower surface of the first top wall of the first table flange acceptor.

18. The method of claim 17, wherein positioning the second table flange within the second table flange acceptor comprises positioning a second vertical shaft of the second table flange within a second Y-shaped opening of a second top wall of the second table flange acceptor, the second vertical shaft coupled to a second lower flange part of the second table flange, the second lower flange part having a second upper surface that is in face-sharing contact with a second lower surface of the second top wall of the second table flange acceptor.

19. The method of claim 16, wherein the first table flange and the second table flange are positioned at the bottom end of the patient table and the top end of the patient table is coupled to the bore of the mobile imaging system when the table support is coupled to the patient table, when the patient table is lowered to the second position, and when the first locking clamp is locked to the first floor panel and the second locking clamp is locked to the second floor panel.

20. The method of claim 16, further comprising locking one or more wheels of the patient table by positioning a braking block of the table support within a groove of a brake pedal of the patient table.

* * * * *